United States Patent [19]

Holland et al.

[11] Patent Number: 4,680,415

[45] Date of Patent: Jul. 14, 1987

[54] INTERMEDIATES FOR 7-FLUORO DIHYDRO PGI COMPOUNDS

[75] Inventors: George W. Holland, North Caldwell; Hans Maag, Upper Montclair; Perry Rosen, North Caldwell, all of N.J.

[73] Assignee: Hoffmann-La Roche Inc., Nutley, N.J.

[21] Appl. No.: 885,993

[22] Filed: Sep. 8, 1986

Related U.S. Application Data

[62] Division of Ser. No. 747,740, Jun. 24, 1985, Pat. No. 4,634,782.

[51] Int. Cl.⁴ ........................................ C07D 307/935
[52] U.S. Cl. ................................................ 549/214
[58] Field of Search ........................................ 549/214

[56] References Cited

U.S. PATENT DOCUMENTS 4,558,142  12/1985  Holland et al. ..................... 549/465

FOREIGN PATENT DOCUMENTS 0054795  6/1982  European Pat. Off. .
0148953  7/1985  European Pat. Off. .
2088856  7/1982  United Kingdom .
2094310  9/1982  United Kingdom .

Primary Examiner—Henry R. Jiles
Assistant Examiner—Bernard I. Dentz
Attorney, Agent, or Firm—Jon S. Saxe; George M. Gould; William H. Epstein

[57] ABSTRACT

7-fluoro-16-substituted 15-hydroxy PGI$_2$ compounds which have saturated bond of the 13 position and which are useful as blood platelet anti-aggregating agents.

8 Claims, No Drawings

INTERMEDIATES FOR 7-FLUORO DIHYDRO PGI COMPOUNDS

CROSS REFERENCE TO RELATED APPLICATION

This application is a divisional of U.S. application, Ser. No. 747,740, filed June 24, 1985—Holland et al, now U.S. Pat. No. 4,634,782, issued Jan. 6, 1987.

BACKGROUND AND STATEMENT OF PRIOR ART

Prostacyclin ($PGI_2$) is a potent vasodilator and a potent inhibitor of platelet aggregation. These properties are opposite to those produced by thromboxane $A_2$ ($TXA_2$) which like $PGI_2$ is a major metabolite of the prostaglandin endoperoxides $PGH_2$ and $PGG_2$. Generally, prostacyclins in vivo prevent the attachment of platelet aggregates to blood vessel walls thereby inhibiting blood platelet aggregation while also lowering blood pressure.

7-halo $PGI_2$ derivatives have been described and found useful for inhibiting blood platelet aggregation while lowering blood pressure. See for example British Patent Application No. 2,094,310—Holland, Maag and Rosen published Sept. 15, 1982; British Patent Application No. 2,088,856—Szekely et al. published June 19, 1982 and U.S. Pat. No. 4,472,428—Toru et al. issued Sept. 18, 1984.

Prostacyclins as therapeutic agents suffer from the inherent disadvantage that they contain a labile enol ether moiety which causes instability. In addition prostacyclins can be used both for their blood pressure lowering and platelet anti-aggregation effect. Therefore, a prostacyclin which is stable and which provides a separation between the anti-aggregation property and the blood pressure lowering effect is ideally suited for use as a therapeutic agent.

SUMMARY OF INVENTION

In accordance with this invention, compounds of the formula

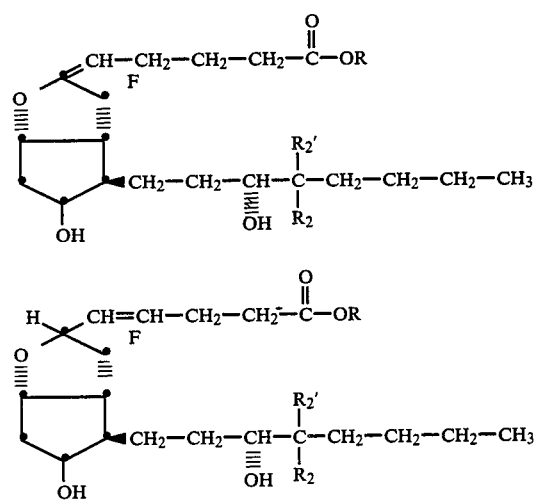

wherein R is hydrogen or lower alkyl; $R_2$ is hydrogen, methyl or fluoro; and $R_2'$ is fluoro, hydrogen, trifluoromethyl or methyl; and with the proviso that when $R_2'$ is trifluoromethyl, $R_2$ is hydrogen or methyl and salts thereof as well as optical antipodes and racemates thereof are useful as a blood platelet anti-aggregating agents. In particular, the compounds of formulae I-A provide a separation of properties since they exhibit strong a blood platelet anti-aggregating affects without substantially reducing blood pressure. In addition, these compounds show a high degree of stability.

The compounds of formulae I-A and I-B are prepared from compounds of the formula:

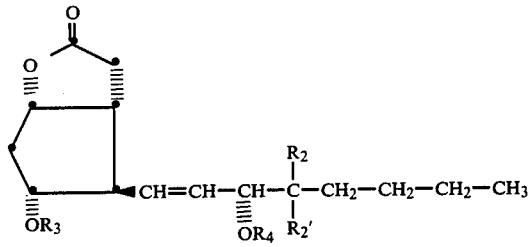

wherein $R_2$ and $R_2'$ are as above; $R_3$ and $R_4$ individually are hydrogen or when taken together with their attached oxygen atom form an ether or ester protecting group;

or optical antipodes or racemates thereof.

DETAILED DESCRIPTION OF THE INVENTION

As used throughout this application, the term "lower alkyl" includes both straight chain and branched chain alkyl groups having from 1 to 7 carbon atoms such as methyl and ethyl. As also used herein, the term "lower alkanoic acids" comprehends an alkanoic acid of 1 to 7 carbon atoms such as formic acid and acetic acid. As further used herein, the the term "halogen" or "halo", unless otherwise stated, comprehends fluorine, chlorine, bromine and iodine. Alkali metal includes all alkali metals such as lithium, sodium and potassium.

In the process of this invention, all compounds having one or more asymmetric carbon atoms can be produced as racemic mixtures. These racemic mixtures which are obtained can be resolved at the appropriate steps in the process of this invention by methods well known in the art whereupon subsequent products may be obtained as the corresponding optically pure enantiomers. On the other hand, the claimed optically active enantiomer or racemates of formula I can be produced depending upon the optical form of the compound of formula II utilized as a starting material.

In the pictorial representation of the compounds given throughout this application, a thickened taper line (——■) indicates a substituent which is in the beta-orientation (above the plane of the molecule), a dotted line (·· ·· ··) indicates a substituent which is in the alpha-orientation (below the plane of the molecule) and a wavy line (∼∼∼) indicates a substituent which is in either the alpha- or beta-orientation or mixtures of these isomers. It is to be understood that the pictorial representations of the compounds given throughout the specification are set forth for convenience and are to be construed as inclusive of other forms including enantiomers and racemates and are not to be construed as limited to the particular form shown.

As also used herein, the term "aryl" signifies mononuclear aromatic hydrocarbon groups such as phenyl, which can be unsubstituted or substituted in one or more positions with a lower alkylenedioxy, nitro, halo, a lower alkyl or a lower alkoxy substituent, and polynuclear aryl groups such as naphthyl, anthryl, phenanthryl, azulyl, etc., which can be unsubstituted or substituted with one or more of the aforementioned groups. The preferred aryl groups are the substituted and unsubstituted mononuclear aryl groups, particularly phenyl.

The term "ether protecting group removable by acid catalyzed cleavage" designates any ether which, upon acid catalyzed cleavage yields the hydroxy group. A suitable ether protecting group is, for example, the tetrahydropyranyl ether, or 4-methoxy-tetrahydropyranyl ether. Others are arylmethyl ethers such as benzyl, benzylhydryl, or trityl ethers or alpha-lower alkoxy lower alkyl ether, for example, methoxymethyl or tri(-lower alkyl)silyl ethers such as trimethyl silyl ether; diphenyl-t-butyl silyl ether or dimethyl-tert-butyl silyl ethers. The preferred ether protecting groups which are removed by acid catalyzed cleavage are t-butyl and tetrahydropyranyl and the tri(lower alkyl and/or aryl)-silyl ethers, particularly dimethyl-tert-butyl silyl ether and diphenyl-t-butyl silyl ether. Acid catalyzed cleavage is carried out by treatment with an organic or inorganic acid. Among the preferred inorganic acids are the mineral acids such as sulfuric acid, hydrohalic acid, etc. Among the preferred organic acids are lower alkanoic acids such as acetic acid, para-toluene sulfonic acid, etc. The acid catalyzed cleavage can be carried out in an aqueous medium or in an organic solvent medium. Where an organic acid or alcohol is utilized, the organic acid or alcohol can be the solvent medium. In the case of tetrahydropyranyl ethers, the cleavage is generally carried out in an aqueous medium. In carrying out this reaction, temperature and pressure are not critical and this reaction can be carried out at room temperature and atmosphere pressure.

The term "ester protecting group" describes ester protecting groups where the hydroxy substituent is protected by esterification with an organic acid to form a hydrolizable ester. Among the preferred esters which can be utilized to protect the hydroxy group are those esters formed by reacting the hydroxy group with a lower alkanoic acid containing from 1 to 7 carbon atoms present as acetic acid, propionic acid, butyric acid, as well as aroic acids such as benzoic acid and aryl lower alkanoic acids where aryl is defined as above and the lower alkanoic acid contains from 2 to 7 carbon atoms.

That the 7-fluoro prostacyclins are potent blood platelet anti-aggregating agents can be seen when the following compounds
Compound A=(5Z,7beta,9alpha,11alpha,15S)-6,9-epoxy-7-fluoro-11,15-dihydroxy-prost-5-en-1-oic acid monosodium salt; and
Compound B=(5Z,7beta,9alpha,11alpha,15R,16S)-6,9-epoxy-7,16-difluoro-11,15-dihydroxy-prost-5-en-1-oic acid monosodium salt;
were tested against $PGI_2$ for their blood platelet anti-aggregation properties by the standard test described by Professor Born in Nature, 194 927, (1962).

In this test, the ability of the above compounds to inhibit aggregation of blood platelets in 0.45 ml of human platelet rich plasma (PRP) was measured. Aggregation was induced by the addition of any one of arachidonic acid (AA), platelet activating factor (PAF) or collagen. PAF and its synthesis is disclosed by Hirth and Barner in Helv. Chim. Acta. Vol. 65; Fasc. 3, page 1059 (1982) [Compound 1-a on page 1061]. By titration of AA, collagen and PAF at various concentrations in 0.45 ml samples of PRP, the minimum amount of AA, collagen and PAF which produces maximum blood platelet aggregation in a given sample of human platelet rich plasma (PRP) was determined. This minimum amount was used when the compounds set forth above were tested for their ability to inhibit blood platelet aggregation in samples of PRP as described below.

In carrying out the tests, various concentrations of the test compound were added to separate samples of human platelet rich plasma (PRP). To each of these samples of PRP containing a specific concentration of one of the above test compounds, there was added the minimum amount of AA, PAF, or collagen calculated above. The controls are samples of PRP containing no test compound but only the minimum amount of AA, PAF, or collagen determined above. The percent aggregation of the various samples was determined by measuring the optical density of the samples and comparing them with the optical density of the controls. This determination was made two minutes after the maximum first phase response of PAF, AA or collagen. This determination was made with freshly prepared samples of test compounds. A second determination was made in the same manner with samples of PRP two hours after the addition of AA, PAF or collagen. The $IC_{50}$, the dose at which the optical density of the samples decrease to a value which is fifty (50%) percent of the value of the control was determined by the method disclosed in Professor Born's article. The $IC_{50}$ values for the minimum dose were made from concentration response curve. These $IC_{50}$'s were determined in two separate tests using PRP from two separate donors. The results of the minimum dose of each of the test compounds which reduces fifty (50%) percent of the aggregation of the platelets produced by any one of AA, PAF, or collagen is set forth in the following Table:

TABLE 1

| Compound | Aggregation $IC_{50}$ (nm) | | |
|---|---|---|---|
| | AA | PAF | Collagen |
| $PGI_2$ | 0.45 | 0.15 | 2 |
| Compound A | 23 | 15 | — |
| Compound B | 20 | 6 | 6 |

The compounds of formulae I-A and I-B because of their potent blood platelet aggregation inhibiting activity are effective as anti-thrombotic agents and in treating disorders due to blood clotting.

The compounds of this invention possess the property of increasing the levels of cyclic adenosine monophosphate (AMP) produced in blood platelets. Cyclic AMP prevents aggregation of blood platelets. Through increasing cyclic AMP, the compounds of this invention prevent blood platelet aggregation. That the compounds of this invention increase cyclic AMP can be seen from the following test.

In this test, human platelet rich plasma (PRP) was prepared by centrifugation of blood treated with 0.38% by weight sodium citrate at $180 \times g$ (times gravity) for ten minutes. The PRP (50 ml containing approximately $2 \times 10^7$ platelets) is incubated for two minutes at 22 C., with and without the test compound, in a Tris-HCl buffer for ten minutes pH 7.4 containing 5.5 mM HCl, 1 mM $MgSO_4$, 5 mM $Na_2HPO_4$, 120 mM NaCl, and 5.5 mM glucose in a fluid volume of 250 ml. The reaction was terminated by placing the samples in boiling water for 3 minutes. The boiled extract was assayed for cyclic AMP by the protein binding method of Brown et al. (Biochemical Journal 121:561–562, 1971). The activity of this test compound at 0.1 mM is measured as the percent increase in cyclic AMP production compared to base 1 (vehicle alone) production. The results are given below:

| Compound | Cyclic AMP Production o/o stimulative of Basal at 0.1 mM |
| --- | --- |
| PGI$_2$ | 3721 |
| Compound A | 998 |
| Compound B | 1353 |

The compounds of formulae I-A and I-B and their pharmaceutically acceptable salts because of their stability and their ability to inhibit blood platelet aggregation are effective in alleviating symptoms of periferal vascular diseases.

The compounds of formulae I-A and I-B or their pharmaceutically acceptable salts can be used in a variety of pharmaceutical preparations. In these preparations, these compounds or their salts are administerable in the form of tablets, pills, powders, capsules, injectables, solutions, suppositories, emulsions, dispersions, and in other suitable forms. The pharmaceutical preparations which contain the compounds of formulae I-A and I-B or their pharmaceutically acceptable salts are conveniently formed by admixing them with a non-toxic pharmaceutical organic or inorganic carrier. Typical of pharmaceutically acceptable carriers are, for example, water, gelatin, lactose, starch, magnesium stearate, talc, vegetable oils, polyalkylene glycols, petroleum jelly and other conventionally employed pharmaceutically acceptable carriers. The pharmaceutical preparations may also contain non-toxic auxiliary substances such as emulsifying, preserving and wetting agents and the like, as for example, sorbitan monolaurate, triethanol amine oleate, polyoxyethylene sorbitan, dioctyl sodium sulfosuccinate and the like.

The daily dose administered for the compounds will, of course, vary with the particular novel compound employed because of the very potency of the compounds, the chosen route of administration and the size of the recipient. The dosage administered is not subject to definite bounds but it will usually be in effective amounts of the pharmacologically function of the prostacyclin. Representative of a typical method for administering the prostacyclin compounds of formulae I-A and I-B or pharmaceutically acceptable salts thereof is by oral administration. By this route, the prostacyclins of formulae I-A and I-B or their salts can be administered at a dosage of 0.1 micrograms to 0.50 milligrams per day per kilogram of body weight.

The compounds of formula I-A and I-B and salts thereof and can be administered to the skin in preparations for topical administrations such as solutions, suspensions, ointments, creams, gels, micronized powders, aerosols and the like. The pharmaceutical preparations may be sterilized and/or may contain adjuvants such as preservatives, stabilizers, wetting agents, emulsifiers, salts for varying the osmotic pressure and/or buffers.

For topical administration to the skin the aforementioned compounds or their salts are preferably prepared as ointments, tinctures, creams, gels, solutions, lotions, sprays, suspensions, shampoos, hair soaps, perfumes and the like. In fact, any conventional composition utilized for application to the scalp or skin can be utilized in accordance with this invention. Among the preferred methods of applying the composition containing the agents of this invention is in the form of gel, lotion and cream solutions. The pharmaceutical preparation for topical administration to the skin can be prepared by mixing the aforementioned active ingredient with non-toxic, therapeutically inert, solid or liquid carriers customarily used in such preparations. These preparations should contain at least about 0.0005 percent by weight, of the active ingredient based upon the total weight of the composition. Since the active ingredient, the compound of formula I, is non-toxic, non-teratogenic and non-irritating it may be used in topical compositions in amounts significantly exceeding 10 percent i.e. up to 20% by weight. It is however preferred that these preparations contain about 0.01 to 10 percent by weight of the active ingredient based upon the total weight of the composition. It is also preferred to apply these preparations once or twice daily to the skin. These preparations can be applied according to the need of the patient. In carrying out this invention, the active ingredient can be applied in an aqueous solution or an alcohol solution such as ethyl alcohol.

In preparing the topical preparations described above additives such as preservatives, thickeners, perfumes, and the like conventional in the art of pharmaceutical compounding of topical preparations can be used. In addition, conventional antioxidants or mixtures of conventional antioxidants can be incorporated into the topical preparations containing the aforementioned active agent. Among the conventional antioxidants which can be utilized in these preparations are included N-methyl-a-tocopherolamine, tocopherols, butylated hydroxyanisole, butylatedhydroxytoluene, ethoxyquin and the like. Cream-base pharmaceutical formulations containing the active agent, used in accordance with this invention, are composed of aqueous emulsions containing a fatty acid alcohol, semi-solid petroleum hydrocarbon, 1,2-ethyleneglycol and an emulsifying agent.

Ointment formulations containing the active agent in accordance with this invention comprise admixtures of a semi-solid petroleum hydrocarbon with a solvent dispersion of the active material. Cream compositions containing the active ingredient for use in this invention preferably comprise emulsions formed from a water phase of a humectant, a viscosity sterilizer and water, an oil phase of fatty acid alcohol, a semisolid petroleum hydrocarbon and an emulsifying agent and a phase containing the active agent dispersed in an aqueous stabilizer-buffer solution. Stabilizers may be added to the topical preparation. Any conventional stabilizer can be utilized in accordance with this invention. In the oil phase, fatty acid alcohol components function as a stabilizer. These fatty acid alcohol components are derived from the reduction of a long-chain saturated fatty acid of at least 14 carbon atoms. Also, conventional perfumes and lotions generally utilized in topical preparation for the hair can be utilized in accordance with this invention. Furthermore, if desired, conventional emulsifying agents can be utilized in the topical preparations of this invention.

Among the preferred compound of formulae I-A and I-B are those compounds where the 7-fluoro substituent is in the beta configuration since these compounds are prepared easily in high yields. However, the compounds where the 7-fluoro substituted is in the alpha position are also preferred due to their enhanced stability. Among the 7-beta fluoro compounds, the following are preferred:

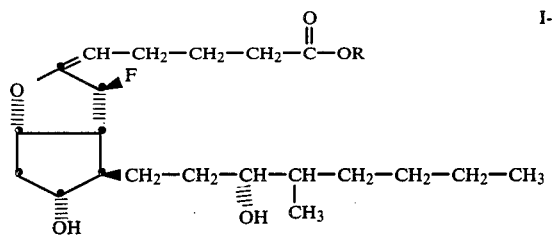

I-Ai

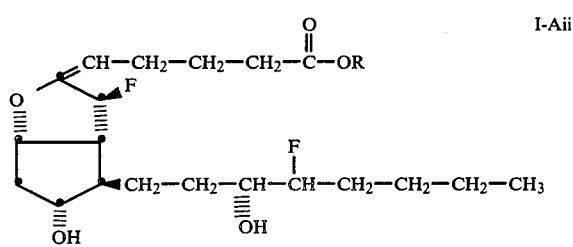

I-Aii where R is hydrogen or lower alkyl

When R is lower alkyl in the compound of formulae I-Ai and I-Aii, R is preferably methyl or ethyl.

In preparing the compounds of this invention, the compound of formula II is converted to a compound of the formula:

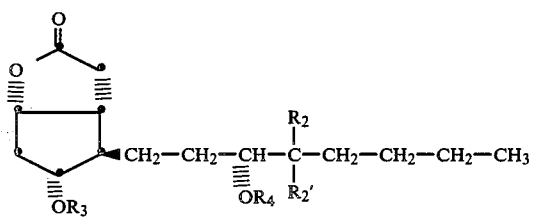

III wherein $R_2$, $R_2'$, $R_3$ and $R_4$ are as above;

by hydrogenation utilizing conventional hydrogenation catalysts such as palladium, rhodium and platinum. In carrying out this reaction any of the conditions conventionally used in catalytic hydrogenation can be used. If desired, this reaction can be carried out with $R_3$ and $R_4$ being hydrogen. On the other hand, one or both of the hydroxyl substituents on the compounds of formula II may be protected with either an ether or an ester protecting group prior to being subjected to hydrogenation to produce the compounds of formula III. In the compound of formulae II and III, $R_3$ and $R_4$ can be any conventional ether or ester protecting group such as the ether protecting groups removable by acid catalyzed cleavage or the ester groups removable by hydrolysis.

In the next step in the production of the compounds of formula I-A and I-B, the compounds of formula III where $R_3$ and $R_4$ are other than a tri(lower alkyl and/or aryl)silyl protecting group are converted to compounds of the formula

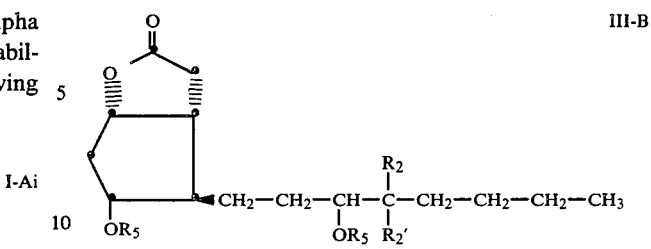

III-B wherein $R_2$ and $R_2'$ are as above; and $R_5$ is tri(lower alkyl and/or aryl)silyl;

Where $R_3$ and $R_4$ in the compound of III are hydrogen, the compound of formula III can be converted to the compound of formula III-B by reaction with a tri(-lower alkyl and/or aryl)halosilane, preferably t-butyldimethyl chlorosilane. Any of the conditions conventional in reacting a hydroxy compound with a halosilane to form a siloxy derivative can be used in carrying out this reaction. Where $R_3$ and $R_4$ in the compound of formula III are a cleavable ether protecting group other than a tri(lower alkyl and/or aryl)silyl group, the protecting group can be cleaved by procedures well known in the art to produce a compound of the formula III where $R_3$ and $R_4$ are hydrogen. On the other hand, where $R_3$ and $R_4$ from a hydrolyzable ester groups, these groups can be hydrolyzed by conventional means to form compounds of formula III where $R_3$ and $R_4$ are hydrogen. These latter compounds can be converted to the compound of formula III-B by reaction with a tri(-lower alkyl and/or aryl)halosilane as described above.

The compounds of formulae I-A and I-B are prepared from the compound of formula III-B via the following intermediates:

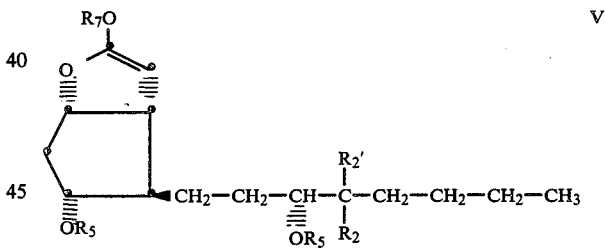

V

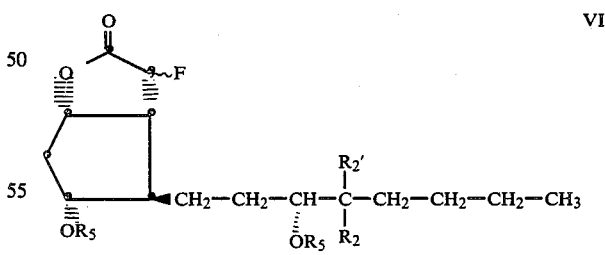

VI

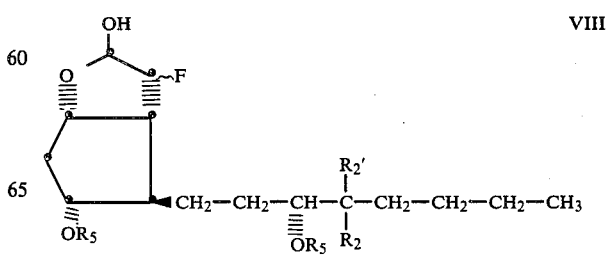

VIII

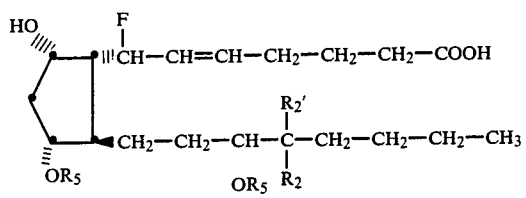

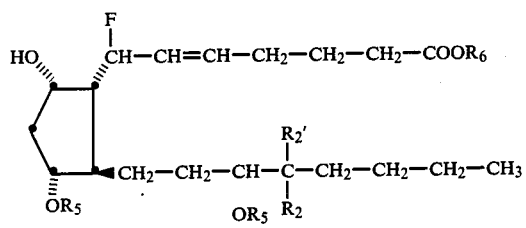

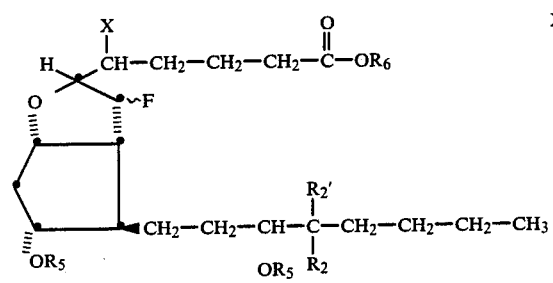

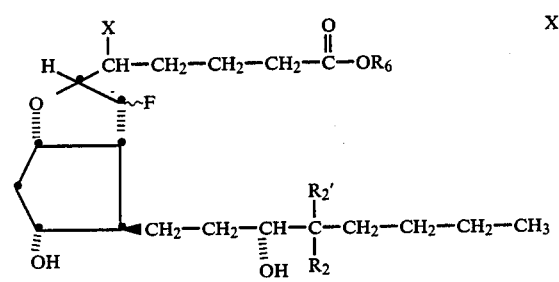

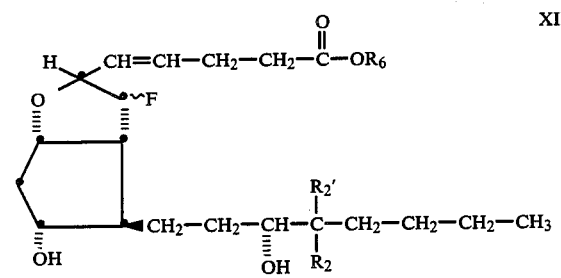

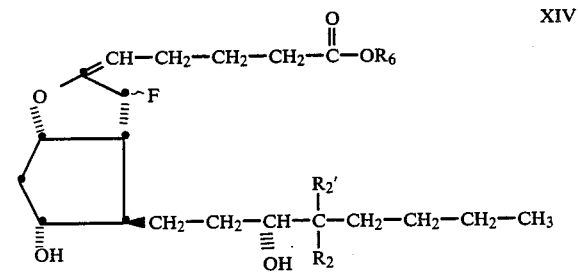

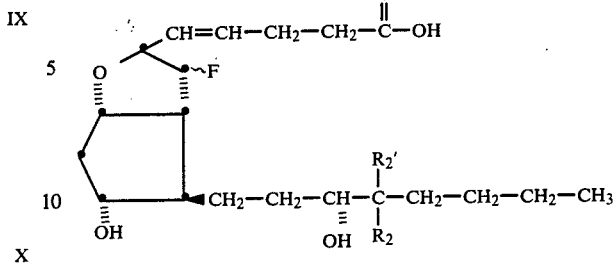

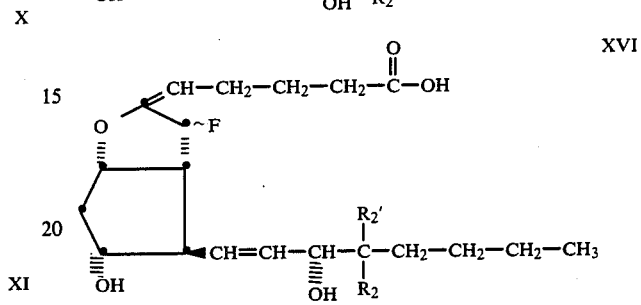

wherein $R_2$, $R_2'$ and $R_5$ are as above; $R_6$ is lower alkyl and X is halogen; and $R_7$ is tri(lower alkyl and/or aryl)silyl.

The compound of formula III-B is converted to the compound of formula V by first enolizing the compound of formula III-B and then treating the enolized form of the compound of formula III-B with a tri(alkyl and/or aryl)halosilane. Any conventional method of enolizing can be utilized to enolize the compound of formula III-B. Among the preferred methods is by treating the compound of formula III-B with a non-aqueous alkali metal base. The preferred base for use in this reaction is lithium diisopropyl amide or sodium hexamethyldisilazane. In carrying out the reaction utilizing the non-aqueous alkali metal base, temperatures of $-70°$ C. to $30°$ C. are generally preferred. Generally, this reaction is carried out in an inert organic solvent. Any conventional inert organic solvent which is a liquid at the aforementioned temperatures can be utilized. Among the preferred solvents are tetrahydrofuran. The enolate of the compound of formula III-B in the form of its alkali metal salt is converted to the compound of formula V by treating with a tri(alkyl and/or aryl)-halosilane, preferably trimethylchlorosilane. Generally, this reaction is carried out at the same temperatures and in the same solvent utilized to form the enolate.

The compound of formula V is converted to the compound of formula VI by treating the compound of formula V with a fluorinating agent. Any conventional fluorinating agent can be utilized in carrying out this reaction. Among the preferred fluorinating agents is xenon difluoride. Generally, this reaction is carried out in the presence of an inert organic solvent. Any conventional inert organic solvent can be utilized in carrying out this reaction. Among the preferred solvents are halogenated hydrocarbons such as methylene chloride, carbon tetrachloride, etc. In carrying out this reaction, temperature and pressure are not critical and this reaction can be carried out at room temperature and atmospheric pressure. While room temperature can be utilized, it is preferred to carry out this reaction at low temperatures, i.e. from $-10°$ C. to $+10°$ C.

In converting the compound of formula V to the compound of formula VI, the compound of formula VI is produced as a mixture of the following compounds:

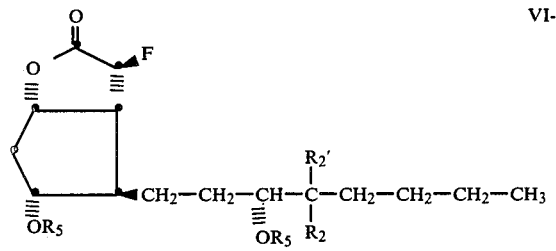

VI-A

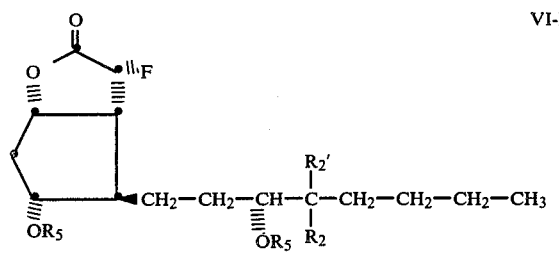

VI-B wherein $R_2$, $R_2'$ and $R_5$ are as above.

The compounds of formulae VI-A and VI-B can be separated by conventional methods such as chromatography. On the other hand, the compound of formula VI as a mixture of the compounds of formulae VI-A and VI-B can be utilized throughout the rest of the reactions or, if desired, separated at some later state in the reaction scheme to produce the compound of formula I-A or I-B having the desired fluoro orientation at the 7-position. If the compound of formula VI is separated into the compound of formulae VI-A and VI-B, the same configuration of the fluorine atom is carried out throughout the rest of the reactions to produce the compounds of formula IA or IB. Therefore, in producing the compounds of formulae I-A or I-B wherein the fluorine atom is at the 7-beta position, the compound of formula VI-A is utilized in the rest of the reaction scheme to produce compounds of the formulae VIII through XVI wherein the 7-fluoro substituent in these formulae is in the beta position. If the compounds of I-A and I-B are desired wherein the fluoro substituent is in the 7-alpha position, then the compound of formula VI-B is utilized in the reaction scheme to produce the compounds of formulae VIII through XVI wherein the fluoro substituent shown in these formulae is in the alpha position.

On the other hand, the compound of formula VI can be utilized without separating into the compounds of formulae VI-A and VI-B. In this manner, the compounds of formulae I-A and I-B wherein the 7-fluoro substituent is in both the alpha and beta positions is produced via intermediates of the formulae VIII through XVI having the 7-fluoro group in both positions as shown.

The compound of formula VI is converted to the compound of formula VIII by treating the compound of formula VI with a reducing agent. In carrying out this reaction, any conventional reducing agent which will selectively reduce a lactone to a lactol can be utilized. Preferred reducing agents are the hydrides, particularly the aluminum hydrides such as alkali metal aluminum hydride, and the borohydrides such as alkali metal borohydrides, with diisobutyl aluminum hydride being particularly preferred. Also, this reaction can be carried out utilizing di(branched chain lower alkyl)boranes such as bis(3-methyl-2-butyl)borane. In carrying out this reaction, temperature and pressure are not critical and the reaction can be carried out at room temperature and atmospheric pressure or at elevated or reduced temperatures and pressures. Generally, it is preferred to carry out this reaction at a temperature of from −80° C. to room temperature. This reduction reaction can be carried out in the presence of an inert organic solvent. Any of the conventional inert organic solvents can be utilized in carrying out this reaction. Among the preferred solvents are dimethoxy ethylene glycol, and the ethers such as tetrahydrofuran, diethyl ether and dioxane.

The compound of formula IX is obtained from the compound of formula VIII by reaction the compound of formula VIII with phosphonium salts of the formula:

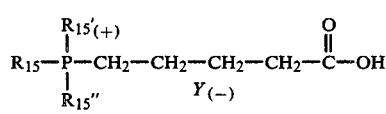

XX-A wherein $R_{15}$, $R_{15}'$, $R_{15}''$ is aryl or di(lower alkyl)amino; and Y is halogen via a conventional Wittig type reaction. Any of the conventional conditions in Wittig reactions can be utilized in carrying out this reaction.

The compound of formula IX can be converted to a compound of the formula X by esterification with diazomethane or a reactive derivative of a lower alkanol such as a lower alkyl halide. Any conventional conditions utilizing in these esterifying reactions can be utilized to form the compound of formula X from the compound of formula IX.

The compound of formula X is converted to the compound of formula XI by treating the compound of formula X with a halogenating agent. Among the preferred halogenating agents are included N-halosuccinimides, particularly N-iodosuccinimide. Generally, this reaction is carried out in the presence of a polar solvent such as acetonitrile and halogenated hydrocarbons such as methylene chloride, ethylene chloride, etc. In fact, any conventional polar organic solvent can be utilized. In carrying out this reaction, temperature of from 0° C. to 35° C. can be utilized. Generally, it is preferred to carry out this reaction at room temperature.

The compound of formula XI is converted to the compound of formula XII by ether cleavage. Any conventional method of ether cleavage described hereinbefore can be utilized to carry out this reaction.

In the next step, the compound of formula XII is treated with a dehydrohalogenating agent to produce the compounds of formulae XIII and XIV in admixture. In carrying out this reaction, any conventional dehydrohalogenating agent can be utilized. Among the preferred dehydrohalogenating agents are the diazabicycloalkanes or alkanes such as 1,8-diazabicyclo[5.4.0]undec-7-ene and 1,4-diazabicyclo[2.2.2]octane. Furthermore, any other conventional organic base utilized for dehydrohalogenation can be utilized in carrying out this reaction. This reaction produces the compounds of formula XIII and the compounds of formula XIV in admixture. The compounds of formula XIII can be separated from the compounds of formula XIV by any conventional separation procedure such as chromatography.

The compound of formula XIII can be converted to the compound of formula XV and the compound of formula XIV is converted to the compound of formula XVI by hydrolysis. Any conventional method of ester hydrolysis can be utilized in carrying out these reactions. Among the preferred method of ester hydrolysis is either treating the compound of formula XIII or the compound of formula XIV with a alkali metal hydroxide. Among the preferred alkali metal hydroxides for use in this reaction are sodium and potassium hydroxides.

In the practice of this invention, any pharmaceutically acceptable basic salts of the compound of formula I-A and I-B where R is hydrogen can be utilized. Among the preferred pharmaceutically acceptable basic salts are included the alkali metal salts such as lithium, sodium, and potassium, with sodium being especially preferred. Other salts which are also preferred are the alkaline earth metal salts such as calcium and magnesium, amine salts such as the lower alkyl amines, e.g. ethylamine and the hydroxy-substituted lower alkyl amine salts and tris(hydroxymethyl)aminomethane. Also preferred are the ammonium salts. Among the other salts are dibenzylamine, monoalkylamines or dialkylamine and salts with amino acids (i.e. salts with arginine and glycine).

The following Examples are illustrative but not limitative of the invention. In the Examples, the ether utilized was diethyl ether. All temperatures are in degrees Centigrade. Celite is diatomaceous earth and DMF is dimethyl formamide.

EXAMPLE 1

[3aR-[3a alpha,4alpha(3S*),5beta,6a alpha]]-5-(Benzoyloxy)Hexahydro-4-(3-Hydroxyoctyl)-2H-Cyclopenta[b]furan-2-one To 2 g of platinum in 100 ml of ethyl acetate was added a solution of 19.8 g of (0.053 mol) of [3aR-[3a alpha,4alpha(1E,3S*),5beta,6a alpha]]-5-(benzoyloxy)-hexahydro-4-(3-hydroxy-1-octenyl)-2H-cyclopenta[b]furan-2-one in 100 ml of ethyl acetate. The solution was then hydrogenated until the theoretical uptake of hydrogen was complete (ca. 2h) and then filtered through a bed of Celite. The solvent was then removed under reduced pressure to give 19.9 g of [3aR-[3a alpha,4alpha(3S*),5beta,6a alpha)]-5-(benzoyloxy)hexahydro-4-(3-hydroxyoctyl)-2H-cyclopenta[b]furan-2-one as colorless oil (100% yield) $[a]_D^{25} -72.03$ (CHCl$_3$, C=0.794).

Anal. Calcd for $C_{22}H_{30}O_5$: C, 70.56, H, 8.80. Found: C, 70.51; H, 7.97.

EXAMPLE 2

[3aR-[3a alpha,4alpha(3R*,4S*),5beta,6a alpha]]-5-(Benzoyloxy)-4-(4-Fluoro-3-Hydroxyoctyl)-Hexahydro-2H-Cyclopenta[b]furan-2-one To 1.1 g of platinum in 50 ml of ethyl acetate was added a solution of 11 g of (0.028 mol) of [3aR-[3a alpha,4alpha(1E,3R*,4S*),5beta,6a alpha]]-5-(benzoyloxy)-4-(4-fluoro-3-hydroxy-1-octenyl)hexahydro-2H-cyclopenta[b]furan-2-one in 110 ml of ethyl acetate. The mixture was then hydrogenated until the theoretical uptake of hydrogen was complete and then filtered through a bed of Celite. The solvent was then removed under reduced pressure and the residue chromatographed over 250 g of silica gel (toluene — α 30% by volume ethyl acetate/70% by volume toluene) to afford 10.7 g of [3aR-[3a alpha,4alpha(3R*,4S*),5beta,6a alpha)]-5-(benzoyloxy)-4-(4-fluoro-3-hydroxyoctyl)hexahydro-2H-cyclopenta[b]furan-2-one (94% yield) as a colorless oil.

Anal. Calcd for $C_{22}H_{29}FO_5$: C, 67.33; H, 7.45. Found: C, 66.80; H, 7.51.

EXAMPLE 3

[3aR-[3a alpha,4alpha(3S*),5beta,6a alpha]]-Hexahydro-5-[[(1,1-Dimethylethyl)Dimethylsilyl]oxy]-4-[3-[[(1,1-Dimethylethyl)Dimethylsilyloxy]octyl]-2H-Cyclopenta[b]furan-2-one To a solution of 20.5 g (0.055 mol) of [3aR-[3a alpha,4alpha-(3S*),5beta,6a alpha]]-5-(benzoyloxy)hexahydro-4-(3-hydroxyoctyl)-2H-cyclopenta-[b]furan-2-one dissolved in 200 ml of methanol was added 14.35 g of Na$_2$CO$_3$. After 4 hr an additional 14.4 g of Na$_2$CO$_3$, was added and then again 3 hr later. The mixture was then filtered and the Na$_2$CO$_3$, washed with dry methanol. The methanol was removed under reduced pressure and the residue dissolved in ethyl acetate. The ethyl acetate solution was washed with water; the water layer saturated with NaCl and extracted with additional ethyl acetate. The ethyl acetate solutions were combined and dried (MgSO$_4$). The solvent was then removed under reduced pressure and the residue chromatographed on 400 g of silica gel (5% by volume ethyl acetate/95% by volume hexane — α ethyl acetate) to give 11 g of the diol, i.e. 3aR-[3a alpha,4alpha(3S*),5beta,6a alpha]]-5-hydroxy-4-(3-hydroxyoctyl)-2H-cyclopenta[b]furan-2-one.

To 10.2 g of the diol dissolved in 150 ml of DMF was added 13.1 g of imidazole followed by 23.4 g of t-butyl-dimethylchlorosilane and the reaction mixture stirred for 18 hr. The mixture was then added to 500 ml of 0.5N NH$_4$Cl solution and the mixture extracted with 3×500 ml of ether. The combined ether extracts were washed with a saturated NaHCO$_3$ solution followed by a saturated NaCl solution. The ether solution was then dried (MgSO$_4$), the ether removed under reduced pressure and the residue chromatographed on 500 g of silica gel (10% by volume ether/90% by volume petroleum ether — α 20% by volume ether/80% by volume petroleum ether) to give 13.6 g of [3aR-[3a alpha,4alpha(3S*),5beta,6a alpha]]hexahydro-5-[[(1,1-dimethylethyl)dimethylsilyl]oxy]-4-[3-[[(1,1-dimethylethyl)dimethylsilyloxy]octyl]-2H-cyclopenta[b]furan-2-one as a colorless oil.

Anal. Calcd for $C_{27}H_{54}O_4Si_2$: C, 65.00; H, 10.91. Found: C, 64.84; H, 11.03.

EXAMPLE 4

[3aR-[3a alpha,4alpha(3R*,4S*),5beta,6a alpha]]-Hexahydro-4-(4-fluoro-3-hydroxyoctyl)-5-hydroxy-2H-cyclopenta[6]furan-2-one To a solution of 10.3 g (0.026 mol) of [3aR-[3a alpha,4alpha(3R*,4S*),5beta,6a alpha]]-hexahydro-5-(benzoyloxy)-4-(4-fluoro-3-hydroxyoctyl)2H-cyclopenta[b]furan-2-one dissolved in 200 ml of CH$_3$OH was added 7 g of Na$_2$CO$_3$. After several hours an additional 5 g of Na$_2$CO$_3$ was added and the mixture allowed to stir overnight. The mixture was filtered and the solvent removed under reduced pressure. The residue was dissolved in CH$_2$Cl$_2$, dried (MgSO$_4$), and the solvent removed under reduced pressure. The resulting solid was then triturated with a small amount of cold ether to give 5.5 g (73.3% yield) of [3aR-[3a alpha,4alpha(3R*,4S*),-5beta,6a alpha]]-hexahydro-4-(4-fluoro-3-hydroxyoctyl)-5-hydroxy-2H-cyclopenta[b]furan-2-one as white crystals: mp 99°-100° C.; $[a]_D^{25}$ −18.86 (CHCl$_3$, C=1.0).

Anal. Calcd for C$_{15}$H$_{25}$FO$_4$: 6, 62.48; H, 8.74. Found: C, 62.48; H, 8.67.

EXAMPLE 5

[3aR-[3a alpha,4alpha(3R*,4S*),5beta,6a alpha]]-Hexahydro-5-[[(1,1-Dimethylethyl)Dimethylsilyl]oxy]-4-[[[3-(1,1-Dimethylethyl)Dimethylsilyl]oxy]-4-Fluorooctyl]-2H-Cyclopenta[b]furan-2-one To a solution of 6.0 g (0.0208 mol) of [3aR-[3a alpha,-4alpha(3R*,4S*),5beta,6a alpha]]-hexahydro-4-(4-fluoro-3-hydroxy-octyl)-5-hydroxy-2H-cyclopenta[b]furan-2-one dissolved in 100 ml of dry DMF was added 7.2 g of imidazole and 12.9 g of t-butyldimethylchlorosilane. After 18 hr the reaction mixture was poured into 500 ml of 0.5N cold (0° C.) HCl and the mixture extracted with ether. The ether extract was washed with a saturated NaHCO$_3$, solution followed by a saturated NaCl solution. The ether solution was then dried and the solvent removed under reduced pressure. Chromatography on silica gel (2% by volume ethyl acetate/98% by volume hexane − ∝ 20% by volume ethyl acetate/80% by volume hexane) afforded 9.5 g (85.4% yield) of [3aR-[3a alpha,4alpha(3R*,4S*),5beta,6a alpha]]-hexahydro-5-[[(1,1-dimethylethyl)dimethylsilyl]oxy]-4-[[[3-(1,1-dimethylethyl)dimethylsilyl]oxy]-4-fluorooctyl]-2H-cyclopenta[b]furan-2-one; $[a]_D^{25}$ −30.13 (CHCl$_3$, C=1.08).

Anal. Calcd for C$_{27}$H$_{53}$FO$_4$Si$_2$: C, 62.74; H, 10.34. Found: C, 62.88; H, 10.56.

EXAMPLE 6

[3S-[3alpha,3a alpha,4alpha(3S*),5beta,6a alpha]]-3-Hexahydro-3-fluoro-5-[[(1,1-Dimethylethyl)-Dimethylsilyl]oxy]-4-[3-[[(1.1-Dimethylethyl)dimethylsilyl]oxy]octyl]-2H-Cyclopenta[b]furan-2-one To a solution of 4.5 ml of diisopropylamine in 50 ml of dry THF (tetrahydrofuran) cooled to 0° C. was added dropwise over a period of twenty minutes 19.6 ml of n-butyllithium (1.5M in hexane). After stirring an additional five minutes at 0° C. the solution was cooled to −40° C. (dry ice/acetone) after which time a solution of 13.1 g (0.0263 mol) of [3aR-[3a alpha,4alpha(3S*),5beta,6a alpha]]-hexahydro-5-[[(1,1-dimethylethyl)dimethylsilyl]oxy]-4-[3-[[(1,1-dimethylethyl)-dimethylsilyl]oxy]octyl]-2H-cyclopenta[b]furan-2-one dissolved in 100 ml of THF was added slowly while maintaining the temperature at −40° C. After five minutes at this temperature 4.5 ml of trimethylchlorosilane was added rapidly. The cooling bath was then removed and the reaction allowed to warm to 15° C. The solvent was then removed under vacuum and the residue treated with 50 ml of dry ether. The mixture was then filtered through a cintered glass filter and the solvent evaporated under high vacuum to produce [3aR-[3a alpha,4alpha(3S*),5beta,6a alpha]]-4,5,6,6a-tetrahydro-5-[[(1,1-dimethylethyl)dimethylsilyl]oxy]-4-[3-[[1,1-dimethylethyl)dimethylsilyl]oxy]-octyl]-2-[(trimethylsilyl)oxy]-3aH-cyclopenta[b]furan. This compound was then dissolved at 0° C. in 50 ml of dry CH$_2$Cl$_2$ containing 5.26 g of KHCO$_3$, followed by the slow addition of 5.0 g of xenon difluoride. The mixture was then stirred for an additional 0.5 hr at 0° C. and then poured into 500 ml of ice water followed by extraction with CH$_2$Cl$_2$. The organic layer was separated, dried, and the solvent removed under reduced pressure. The residue (9.1 g) was then chromatographed on 500 g of silica gel (2% by volume ethyl acetate/98% by volume petroleum ether to 10% ethyl acetate/90% by volume petroleum ether) and afforded 2.2 g of starting material and 7 g (51.5% yield) of [3S-[3alpha,3a alpha,4alpha(3S*),5beta,6a alpha]]-hexahydro-3-fluoro-5-[[(1,1-dimethylethyl)dimethylsilyl]oxy]-4-[3-[[(1,1-dimethylethyl)dimethylsilyl]oxy]octyl]-2H-cyclopenta[b]furan-2-one as a colorless liquid $[a]_D^{25}$ −29.35 (CHCl$_3$, C=0.726).

Anal. Calcd for C$_{27}$H$_{53}$FO$_4$Si$_2$: C, 62.74; H, 10.34. Found: C, 62.94; H, 10.16.

EXAMPLE 7

[3S-[3alpha,3a alpha,4alpha(3R*,4S*),5beta,6a alpha]]-Hexahydro-3-Fluoro-5-[[(1,1-dimethylethyl)-dimethylsilyl]oxy]-4-[[[3-(1,1-Dimethylethyl)dimethylsilyl]oxy]-4-Fluorooctyl]-2H-Cyclopenta[b]furan-2-one To a solution of 4.4 g of lithium hexamethyldisilazide in 100 ml of dry THF under argon at −70° C. was added dropwise to a solution of 9.0 g (0.0174 mol) of [3aR-[3a alpha,4alpha(3R*,4S*),5beta,6a alpha]]-hexahydro-5-[[(1,1-dimethylethyl)dimethylsilyl]oxy]-4-[[[3-(1,1-dimethylethyl)dimethylsilyl]oxy]-4-fluorooctyl]-2H-cyclopenta[b]furan-2-one dissolved in 100 ml of dry THF. After stirring for thirty minutes at −70° C. the temperature was allowed to rise to −45° C. at which time 3.8 ml of trimethylchlorosilane was added over a five-minute period. The cooling bath was then removed and the reaction mixture slowly warmed to room temperature. The THF was then removed under high vacuum to produce [3aR-[3a alpha,4alpha(3R*,4S*),-5beta,6a alpha]]-4,5,6,6a-tetrahydro-5-[[(1,1-dimethylethyl)dimethylsilyl]oxy]-4-[[[3-(1,1-dimethylethyl)-dimethylsilyl]oxy]-4-fluorooctyl]-3aH-cyclopenta[b]furan as a residue. This residue was dissolved in 100 ml of dry CH$_2$Cl$_2$ at 0° C. To the solution was then added 3.5 g KHCO$_3$, followed by the slow addition of 3.2 g of xenon difluoride. At the completion of the addition, the reaction mixture was stirred for an additional ten minutes and then poured into a mixture of 250 ml of saturated NaHCO$_3$, containing 1 g of Na$_2$S$_2$O$_3$.5H$_2$O and 500 ml of ether. The aqueous layer was separated and extracted with ether. The ether solutions were combined, washed with a saturated NaCl solution, dried (MgSO$_4$) and the solvent removed under reduced pressure. The residue was then chromatographed on 250 g of silica gel (2% by volume ethyl acetate/98% by volume hexane to 3% by volume ethyl acetate/97% by volume hexane) to give 6.2 g (66.7% yield) of [3S-[3alpha,3a alpha,4alpha(3R*,4S*),-5beta,6a alpha]]hexahydro-3-fluoro-5-[[(1,1-dimethylethyl)-dimethylsilyl]oxy]-4-[[[3-(1,1-dimethylethyl)dimethylsilyl]oxy]-4-fluorooctyl]-2H-cyclopenta[b]furan-2-one as a colorless oil. $[a]_D^{25}$ −37.38 (CHCl$_3$, C=0.7).

Anal. Calcd for C$_{27}$H$_{52}$F$_2$O$_4$Si$_2$: C, 60.63; H, 9.80. Found: C, 60.41; H, 9.60.

EXAMPLE 8

[3S-[3alpha,3a alpha,4alpha(3S*),5beta,6a alpha]]-Hexahydro-3-Fluoro-5-[[(1,1-Dimethylethyl)-dimethylsilyl]oxy]-4-[3-[[(1,1-Dimethylethyl)dimethyl-silyl]oxy]octyl]-2H-Cyclopenta[b]furan-2-ol To a solution of 7.3 g (0.0141 mol) of [3S-[3alpha,3a alpha,4alpha-(3S*),5beta,6a alpha]]-hexahydro-3-fluoro-5-[[(1,1-dimethylethyl)dimethylsilyl]oxy]-4-[3-[[(1,1-dimethylethyl)dimethylsilyl]oxy]octyl]-2H-cyclopenta[b]furan-2-one cooled to −70° C. was added dropwise 14 ml of diisobutylaluminum hydride (25 wt. %, 1.5M) in toluene. The solution was allowed to stir an additional twenty minutes at −70° C. after which time 20 ml of a saturated NH$_4$Cl solution was added slowly. The mixture was then warmed to 15° C. diluted with 200 ml of ethyl acetate and washed with a saturated NaCl solution. The washings were extracted with ethyl acetate. The ethyl acetate solutions were combined and dried (MgSO$_4$). Removal of the solvent under reduced pressure afforded 7.2 g of residue which was chromatographed over 500 g of silica gel (10% by volume ethyl acetate/90% by volume petroleum ether) to give 6.3 g (86.1% yield) of [3S-[3alpha,3a alpha,4alpha(3S*),-5beta,6a alpha]]-hexahydro-3-fluoro-5-[[(1,1-dimethylethyl)dimethylsilyl]oxy]-4-[3-[[(1,1-dimethylethyl)dimethylsilyl]oxy]octyl]-2H-cyclopenta[b]furan-2-ol as a colorless oil. [a]$_D^{25}$−17.27 (CHCl$_3$, C=0.956).

Anal. Calcd for C$_{27}$H$_{55}$FO$_4$Si$_2$: C, 62.50; H, 10.68. Found: C, 62.16; H, 10.62.

EXAMPLE 9

[3S-[3alpha,3a alpha,4alpha(3R*,4S*),5beta,6a alpha]]-Hexahydro-3-Fluoro-5-[[(1,1-Dimethylethyl)-dimethylsilyl]oxy]-4-[[[3-(1,1-Dimethylethyl)dimethyl-silyl]oxy]-4-Fluorooctyl]-2H-Cyclopenta[b]furan-2-ol By the procedure of example 8, [3S-[3alpha,3a alpha,-4alpha(3R*,4S*),5beta,6a alpha]]-hexahydro-3-fluoro-5-[[(1,1-dimethylethyl)dimethylsilyl]oxy]-4-[[[3-(1,1-dimethylethyl)dimethylsilyl]oxy]-4-fluorooctyl]-2H-cyclopenta[b]-furan-2-one 6.2 g (0.0116 mol) was converted to 6 g (80.6% yield) of [3S-[3alpha,3a alpha,4alpha(3R*,4S*),5beta,6a alpha]]hexahydro-3-fluoro-5-[[(1,1-dimethylethyl)dimethylsilyl]oxy]-4-[[[3-(1,1-dimethylethyl)dimethylsilyl]oxy]-4-fluorooctyl]2H-cyclopenta[b]furan-2-ol obtained as a colorless oil [a]$_D^{25}$−27.38 (CHCl$_3$, C=0.913).

Anal. Calcd for C$_{27}$H$_{54}$F$_2$O$_4$Si$_2$: C, 60.40; H, 10.14. Found: C, 60.35; H, 9.99.

EXAMPLE 10

(5R,6R,7beta,9alpha,11alpha,15S)-6,9-Epoxy-7-Fluoro-11,15-Dihydroxy-5-Iodo-Prostanoic Acid Methyl Ester and
(5S,6S,7beta,9alpha,11alpha,15S)-6,9-Epoxy-7-Fluoro-11,15-Dihydroxy-5-Iodo-prostanoic Acid Methyl Ester To a mixture of 15 g (0.0338 mol) of (4-carboxybutyl) triphenylphosphonium bromide (dried under high vaccum at 100° C. for 18 hr) and 13.5 g (0.0736 mol) of sodium hexamethyldi-silazane under argon was added 200 ml of dry THF followed by 13.4 ml of freshly distilled hexamethylphosphoramide. The resulting orange-red suspension was stirred at room temperature for 1 hr. To this mixture was then added 6.3 g (0.0122 mol) of [3S-[3alpha,3a alpha,4alpha(3S*),5beta,6a alpha]]-hexahydro-3-fluoro-5-[[(1,1-dimethylethyl)dimethylsilyl]oxy-4-[3-[[(1,1-dimethylethyl)dimethylsilyl]oxy]octyl]-2H-cyclopenta[b]furan-2-ol dissolved in 100 ml of dry THF. The resulting yellow-orange mixture was allowed to stir overnight after which time glacial acetic acid was added dropwise until the mixture became colorless. The mixture was then partitioned between 500 ml of ether and 300 ml of H$_2$O at 0° C. and then treated with 1N HCl to pH 3. The layers were separated and the water washed with a saturated NaCl solution and dried (MgSO$_4$).

The ether was then removed under reduced pressure to give 15 g of a light yellow oil containing (5Z,7R,9alpha,11alpha,15S)-7-fluoro-11,13-bis-[[(1,1-dimethylethyl)dimethylsilyl]oxy]prost-5-en-1-oic acid. The crude acid was then taken up in 50 ml of dry CH$_2$Cl$_2$ and treated with an ethereal solution of diazomethane. The excess diazomethane was blown off with a stream of argon. The residue was taken up in ether, dried (MgSO$_4$), and the solvent removed under reduced pressure. Chromatography over 500 g silica gel (2% ethyl acetate/98% by volume petroleum ether to 20% acetate/80% by volume petroleum ether) afforded 5 g of (5Z,7R,9alpha,11alpha,15S)-7-fluoro-11,15-bis[[(1,1-dimethylethyl)dimethylsilyl]oxy]prost-5-en-1-oic acid methyl ester.

To a solution of 6.0 g of the methyl ester prepared above in 120 ml of dry acetonitrile was added 16.5 g of N-iodosuccinimide and the resulting mixture stirred 18 hr at room temperature in the absence of light. The mixture was then treated with 500 ml of ether and the resulting solution washed with a 10% by weight aqueous solution of Na$_2$S$_2$O$_3$. The washings were back extracted with ether. The ether solutions were combined and dried (MgSO$_4$). The solvent was then removed under reduced pressure to produce a mixture of (5R,6R,7beta,9alpha,11alpha,15S)-6,9-epoxy-7-fluoro-11,15-bis[[(1,1-dimethylethyl)dimethylsilyl]oxy)-5-iodo-prostanoic acid methyl ester and (5S,6S,7beta,9alpha,11alpha,15S)-6,9-epoxy-7-fluoro-11,15-bis[[(1,1-dimethylethyl)dimethylsilyl]oxy]-5-iodo-prostanoic acid methyl ester as a residue. This residue was then treated with a mixture of 60 ml of THF, 120 ml of glacial acetic acid and 60 ml of water. The mixture was warmed to 50° C. for 18 hr and the solvent removed under high vacuum. The residue, 6.7 g was then chromatographed over 500 g. of silica gel (ether to 50% by volume ether/50% by volume ethyl acetate) to afford 2.9 g of a mixture of (5R,6R,7beta,9alpha,11alpha,15S)-6,9-epoxy-7-fluoro-11,15-dihydroxy-5-iodo-prostanoic acid methyl ester and (5S,6S,7beta,9alpha,11alpha,15S)-6,9-epoxy-7-fluoro-11,16-dihydroxy-5-iodo-prostanoic acid methyl ester.

Anal, Calcd for C$_{21}$H$_{36}$FIO$_5$: C, 49.03; H, 7.05. Found: C, 49.36; H, 7.04.

EXAMPLE 11

A Mixture of
[5S,6S,7beta,9alpha,11alpha,15R,16S]-6,9-Epoxy-7,16-Difluoro-11,15-Dihydroxy-5-Iodo-prostanoic Acid Methyl Ester; and
(5R,6R,7beta,9alpha,11alpha,15R,16S)6,9-Epoxy-7,16-Difluoro-11,15-Dihydroxy-5-Iodo-prostanoic Acid Methyl Ester By the procedure of Example 10, [3S-[3alpha,3a alpha,4alpha(3R*,4S*),5beta,6a alpha]]-hexahydro-3-fluoro-5-[[(1,1-dimethylethyl)dimethylsilyl]oxy]-4-[[[3-(1,1-dimethylethyl)dimethylsilyl]oxy]-4-fluorooctyl]-2H-cyclopenta[b]furan-2-ol 4.6 g (0.0086 mol) was converted to 2 g of a mixture of (5S,6S,7beta,9alpha,11alpha,15R,16S)-6,9-epoxy-7,16-difluoro-11,15-dihydroxy-5-iodo-prostanoic acid methyl ester and (5R,6R,7beta,9alpha,11alpha,15R,16S)-6,9-epoxy-7,16-difluoro-11,15-dihydroxy-5-iodo-prostanoic acid methyl ester via the following intermediates:

(5Z,7R,9alpha,11alpha,15R,16S)-7,16-difluoro-11,15-bis[[(1,1-dimethylethyl)dimethylsilyl]oxy]-prosta-5-en-1-oic acid, (5Z,7R,9alpha,11alpha,15R,16S)-7,16-difluoro-11,15-bis[[(1,1-dimethylethyl)dimethylsilyl]oxy]-prosta-5-en-1-oic acid methyl ester; and A mixture of (5R,6R,7beta,9alpha,11alpha,15R,16S)-6,9-epoxy-7,16-difluoro-11,15-bis[[(1,1-dimethylethyl)dimethylsilyl]oxy]-5-iodo-prostanoic acid methyl ester; and (5S,6S,7beta,9alpha,11alpha,15R,16S)-6,9-epoxy-7,16-difluoro-11,15-bis[[(1,1-dimethylethyl)dimethylsilyl]oxy-prosta-5-en-1-oic acid methyl ester.

EXAMPLE 12

From the mixture produced in Example 11, pure [5S,6S,7beta,9alpha,11alpha,15R,16S]-6,9-epoxy-7,16-difluoro-11,15-dihydroxy-5-iodo-prostanoic acid methyl ester was isolated. $[\alpha]_D^{25} + 14.08$ (CHCl$_3$, C=0.15).

Anal. Calcd for $C_{21}H_{35}F_2IO_5$: C, 47.38; H, 6.63; Found: C, 46.81; H 6.84.

EXAMPLE 13

(5Z,7beta,9alpha,11alpha,15S)-6,9-Epoxy-7-Fluoro-11,15-DiHydroxy-Prost-5-en-1-oic Acid Methyl Ester and
(4E,7beta,9alpha,11alpha,15S)-6,9-Epoxy-7-Fluoro-11,15-Dihydroxy-Prost-4-en-1-oic Acid Methyl Ester To a solution of 2.8 g (0.0054 mol) of (5R,6R,7beta,9alpha,11alpha,15S)-6,9-epoxy-7-fluoro-11,15-dihydroxy-5-iodo-prostanoic acid methyl ester and (5S,6S,7beta,9alpha,11alpha,15S)-6,9-epoxy-7-fluoro-11,15-dihydroxy-5-iodoprostanoic acid methyl ester dissolved in 200 ml of dry toluene was added 5.04 ml of 1,8-diazabicyclo[5.4.0]undec-7-ene (DBU). The solution was then heated under argon at 90° C. for 45 hr. The reaction was then cooled, added to 200 ml of ice water and extracted with 3×250 ml of ether. The ether solutions were combined, washed with a saturated solution of NaCl and dried (MgSO$_4$). The ether was removed under vacuum and the residue (1.9 g) chromatographed over 250 g of silica gel. Elution with 50% by volume ethyl acetate/50% by volume petroleum ether to 75% by volume ethyl acetate/25% by volume petroleum ether afforded 1.2 g of (5Z,7beta,9alpha,11alpha,15S)-6,9-epoxy-7-fluoro-11,15-dihydroxy-prost-5-en-1-oic acid methyl ester as a light yellow oil. $[\alpha]_D^{25} + 59.53$ (CHCl$_3$, C=0.719).

Anal. Calcd for $C_{21}H_{35}FO_5$: C, 65.26; H, 9.12. Found: C, 64.73; H, 8.95.

Continued elution of the column with 100% by volume of ethyl acetate afforded 0.456 g of (4E,7beta,9alpha,11alpha,15S)-6,9-epoxy-7-fluoro-11,15-dihydroxy-prost-4-en-1-oic acid methyl ester as a light yellow oil.

Anal. Calcd for $C_{21}H_{35}FO_5$: C, 65.26; H, 9.12. Found: C, 64.68; H, 9.13.

EXAMPLE 14

(5Z,7beta,9alpha,11alpha,15R,16S)-6,9-Epoxy-7,16-Difluoro-11,15-Dihydroxy-Prost-5-en-1-oic Acid Methyl Ester and
(4E,7beta,9alpha,11alpha,15R,16S)-6,9-Epoxy-7,16-Difluoro-11,15-Dihydroxy-prost-4-en-1-oic Acid Methyl Ester A solution of 2 g of a mixture of (5S,6S,7beta,9alpha,11alpha,15R,16S)-6,9-epoxy-7,16-difluoro-11,15-dihydroxy-5-iodo-prostanoic acid methyl ester and (5R,6R,7beta,9alpha,11alpha,15R,16S)-6,9-epoxy-7,16-difluoro-11,15-dihydroxy-5-iodo-prostanoic acid methyl ester and 20 ml of DBU was allowed to stir under an atmosphere of argon for 20 hr. The mixture was then poured into 200 ml of ice water and extracted with ethyl acetate. The ethyl acetate solution was then washed with a saturated NaCl solution and dried (MgSO$_4$). The solvent was then removed under reduced pressure to give 1.7 g of crude product which was chromatographed on 250 grams of silica gel. Elution with 50% by volume ethyl acetate/50% by volume petroleum ether to 75% by volume ethyl acetate and 25% by volume petroleum ether afforded 0.806 g of (5Z,7beta,9alpha,11alpha,15R,16S)-6,9-epoxy-7,16-difluoro-11,15-dihydroxy-prost-5-en-1-oic-acid methyl ester as a colorless liquid. $[\alpha]_D^{25} + 52.85$ (CHCl$_3$, C=0.42).

Anal. Calcd for $C_{21}H_{34}F_2O_5$: C, 62.36: H, 8.47. Found: C, 62.04; H, 8.46.

Continued elution with 75% by volume ethyl acetate/25% by volume petroleum ether then afforded 0.497 g of (4E,7beta,9alpha,11alpha,15R,16S)-6,9-epoxy-7,16-difluoro-11,15-dihydroxy-prost-4-en-1-oic acid methyl ester as a colorless oil. $[\alpha]_D^{25} + 32.35$ (CHCl$_3$, C=0.22).

Anal. Calcd for $C_{21}H_{34}F_2O_5$: C, 62.36; H, 8.47. Found: C, 61.73; H, 8.61.

EXAMPLE 15

[5Z,7beta,9alpha,11alpha,15R,16S]-6,9-Epoxy-7,16-Difluoro-11,15-Dihydroxy-Prost-5-en-1-oic Acid Sodium Salt To a solution of 53.3 mg (0.00013 mol) of (5Z,7beta,9alpha,11alpha,15R,16S)-6,9-epoxy-7,16-difluoro-11,15-dihydroxy-prost--en-1-oic acid methyl ester in 1 ml of CH$_3$OH, 1 ml of THF and 1 ml H$_2$O under an atmosphere of argon was added 0.131 ml of 1N NaOH. The reaction mixture was allowed to stir at room temperature for 18 hr and the solvent then removed under high vacuum. The residue was then dissolved in 1 ml of ethyl acetate followed by eight drops of methanol. The mixture was then filtered and the residue washed with a solution of eight drops of methanol in 1 ml of ethyl acetate. To the combined ethyl acetate solutions was added 10 ml of hexane and the mixture allowed to remain in the refrigerator for 18 hr. The solvent was then decanted from the oily residue, and the residue then washed with 10 ml of petroleum ether. The residue was then subjected to high vacuum after which it was dissolved in 4 ml of water and lypolized. The resulting solid was then triturated with hexane and dried under vacuum to give 48 mg of (5Z,7beta,9alpha,11alpha,115R,16S)-6,9-epoxy-7,16-difluoro-11,15-dihydroxy-prost--en-1-oic acid sodium salt as a white crystalline solid.

Anal. Calcd for $C_{20}H_{31}F_2NaO_5$: C, 58.24; H, 7.58; F, 9.21. Found: C, 57.54; H, 7.44; F, 9.88.

EXAMPLE 16

(5Z,7beta,9alpha,11alpha,15S)-6,9-Epoxy-7-Fluoro-11,15-Dihydroxyprost-5-en-1-oic Acid Monosodium Salt Monohydrate By the procedure of Example 15, 50 mg of (5Z,7beta,-9alpha,11alpha,15S)-6,9-epoxy-7-fluoro-11,15-dihydroxy-prost-5-en-1-oic acid methyl ester was converted to 26 mg of (5Z,7beta,9alpha,11alpha,15S)-6,9-epoxy-7-fluoro-11,16-dihydroxyprost-5-en-1-oic acid monosodium salt monohydrate (obtained as a white solid).

Anal. Calcd for $C_{20}H_{32}F_2NaO_5 \cdot H_2O$: C, 58.24; H, 8.31; F. 4.61. Found: C, 58.04; H, 8.43; F, 4.45.

EXAMPLE 17

Capsule Formulation

| Ingredient | mg/cap | | | |
|---|---|---|---|---|
| 1. [5Z,7beta,9alpha,11alpha,15R,16S]-6,9-epoxy-7,16-difluoro-11,15-dihydroxy prosten-5-en-1-oic acid sodium salt | 0.01 | 0.5 | 5.0 | 25.0 |
| 2. Lactose Hydrose | 168.99 | 168.5 | 159.0 | 123.0 |
| 3. Corn Starch | 20.0 | 20.0 | 25.0 | 35.0 |
| 4. Talc | 10.0 | 10.0 | 10.0 | 15.0 |
| 5. Mg stearate | 1.0 | 1.0 | 1.0 | 2.0 |
| | 200.0 | 200.0 | 200.0 | 200.0 |

Manufacturing Procedure

1. Mix items 1, 2, and 3 in a suitable mixer for 30 minutes.
2. Add items 4 and 5 and mix for 3 minutes.
3. Fill in suitable capsule.

EXAMPLE 18

Capsule Formulation

| Ingredient | mg/cap | | | |
|---|---|---|---|---|
| 1. (5Z,7beta,9alpha,11alpha,15R,16S)-6,9-epoxy-7-fluoro-11,15-dihydroxy prost-5-en-1-oic acid methyl ester | 0.01 | 0.5 | 5.0 | 25.0 |
| 2. Lactose Hydrose | 168.99 | 168.5 | 159.0 | 123.0 |
| 3. Corn Starch | 20.0 | 20.0 | 25.0 | 35.0 |
| 4. Talc | 10.0 | 10.0 | 10.0 | 15.0 |
| 5. Mg stearate | 1.0 | 1.0 | 1.0 | 2.0 |
| | 200.0 | 200.0 | 200.0 | 200.0 |

Manufacturing Procedure

1. Mix items 1, 2, and 3 in a suitable mixer for 30 minutes.
2. Add items 4 and 5 and mix for 3 minutes.
3. Fill in suitable capsule.

EXAMPLE 19

Capsule Formulation

| Ingredient | mg/cap | | | |
|---|---|---|---|---|
| 1. (5Z,7beta,9alpha,11alpha,15R,16S)-6,9-epoxy-7,16-difluoro-11,15-dihydroxy prost-5-en-1-oic acid methyl ester | 0.01 | 0.5 | 5.0 | 25.0 |
| 2. Lactose Hydrose | 168.99 | 168.5 | 159.0 | 123.0 |
| 3. Corn Starch | 20.0 | 20.0 | 25.0 | 35.0 |
| 4. Talc | 10.0 | 10.0 | 10.0 | 15.0 |
| 5. Mg stearate | 1.0 | 1.0 | 1.0 | 2.0 |
| | 200.0 | 200.0 | 200.0 | 200.0 |

Manufacturing Procedure

1. Mix items 1, 2, and 3 in a suitable mixer for 30 minutes.
2. Add items 4 and 5 and mix for 3 minutes.
3. Fill in suitable capsule.

EXAMPLE 20

Soft Gelatin Capsule Formulation

| Ingredient | mg/cap | | | |
|---|---|---|---|---|
| 1. [5Z,7beta,9alpha,11alpha,15R,16S]-6,9-epoxy-7,16-difluoro-11,15-dihydroxy prosten-5-en-1-oic acid sodium salt | 0.01 | 0.5 | 5.0 | 25.0 |
| 2. PEG 400 (polyethylene glycol molecule at 400) | 149.49 | 149.0 | 194.5 | 374.5 |
| 3. Ascorbyl Palmitate | 0.5 | 0.5 | 0.5 | 0.5 |
| | 150.0 | 150.0 | 200.0 | 400.0 |

Manufacturing Procedure

1. Dissolve item 3 in item 2.
2. Add item 1 to the solution in Step 1 and mix until dissolved.
3. Fill in soft gelatin capsule.

EXAMPLE 21

Capsule Formulation

| Ingredient | mg/cap | | | |
|---|---|---|---|---|
| 1. (5Z,7beta,9alpha,11alpha,15R,16S)-6,9-epoxy-7,16-difluoro-11,15-dihydroxy prost-5-en-1-oic acid methyl ester | 0.01 | 0.5 | 5.0 | 25.0 |
| 2. PEG 400 | 149.49 | 149.0 | 194.5 | 374.5 |
| 3. Ascorbyl Palmitate | 0.5 | 0.5 | 0.5 | 0.5 |
| | 150.0 | 150.0 | 200.0 | 400.0 |

Manufacturing Procedure

1. Dissolve item 3 in item 2.
2. Add item 1 to the solution in Step 1 and mix until dissolved.
3. Fill in soft gelatin capsule.

EXAMPLE 22

Wet Granulation Formulation

| Ingredient | mg/cap | | | |
|---|---|---|---|---|
| 1. [5Z,7beta,9alpha,11alpha,15R,16S]-6,9-epoxy-7,16-difluoro-11,15-dihydroxy prosten-5-en-1-oic acid sodium salt | 0.01 | 0.5 | 5.0 | 25.0 |
| 2. Lactose anhydrose DTG | 106.99 | 106.5 | 102.0 | 118.0 |
| 3. Avicel pH 102 (microcrystalline cellulose) | 15.0 | 15.0 | 15.0 | 25.0 |
| 4. Modified Starch | 7.0 | 7.0 | 7.0 | 10.0 |
| 5. Magnesium stearate | 1.0 | 1.0 | 1.0 | 2.0 |
| | 130.0 | 130.0 | 130.0 | 130.0 |

-continued

| Manufacturing Procedure |
|---|
| 1. Dissolve item 1 in a suitable solvent such as alcohol. |
| 2. Spread the solution in Step 1 over item 2, dry. |
| 3. Add items 3 and 4 and mix for 10 minutes. |
| 4. Add magnesium stearate and mix for 3 minutes and compress |

EXAMPLE 23

Wet Granulation Formulation

| Ingredient | mg/cap | | | |
|---|---|---|---|---|
| 1. (5Z,7beta,9alpha, 11alpha,15R,16S)-6,9-epoxy-7,16-difluoro-11,15-dihydroxy prost-5-en-1-oic acid methyl ester | 0.01 | 0.5 | 5.0 | 25.0 |
| 2. Lactose Anhydrous | 106.99 | 106.5 | 102.0 | 118.0 |
| 3. Avicel pH 102 | 15.0 | 15.0 | 15.0 | 25.0 |
| 4. Modified starch | 7.0 | 7.0 | 7.0 | 10.0 |
| 5. Magnesium stearate | 1.0 | 1.0 | 1.0 | 2.0 |
| | 130.0 | 130.0 | 130.0 | 130.0 |

| Manufacturing Procedure |
|---|
| 1. Dissolve item 3 in item 2. |
| 2. Add item 1 to the solution in Step 1 and mix until dissolved. |
| 3. Fill in soft gelatin capsule. |

EXAMPLE 24

Direct Compression Formulation

| Ingredient | mg/cap | | | |
|---|---|---|---|---|
| 1. [5Z,7beta,9alpha, 11alpha,15R,16S]-6,9-epoxy-7,16-difluoro-11,15-dihydroxy prosten-5-en-1-oic acid sodium salt | 0.01 | 0.5 | 5.0 | 25.0 |
| 2. Lactose Anhydrous DTG[a] | 101.99 | 101.5 | 97.0 | 118.0 |
| 3. Avicel pH 102 | 20.0 | 20.0 | 20.0 | 25.0 |
| 4. Modified starch | 7.0 | 7.0 | 7.0 | 10.0 |
| 5. Magnesium stearate | 1.0 | 1.0 | 1.0 | 2.0 |
| | 130.0 | 130.0 | 130.0 | 130.0 |

| Manufacturing Procedure |
|---|
| 1. Prepare a premix of item 1 with part of item 2. |
| 2. Add the mixture in Step 1 to the mixture of remainder of items 2, 3 and 4 and mix for 10 minutes. Add item 5 and mix for 3 minutes; compress using suitable punch on suitable press. |

EXAMPLE 25

Direct Compression Formulation

| Ingredient | mg/cap | | | |
|---|---|---|---|---|
| 1. (5Z,7beta,9alpha, 11alpha,15R,16S)-6,9-epoxy-7,16-difluoro-11,15-dihydroxy prost-5-en-1-oic acid methyl ester | 0.01 | 0.5 | 5.0 | 25.0 |
| 2. Lactose Anhydrous DTG | 101.99 | 101.5 | 97.0 | 118.0 |
| 3. Avicel pH 102 | 20.0 | 20.0 | 20.0 | 25.0 |
| 4. Modified starch | 7.0 | 7.0 | 7.0 | 10.0 |
| 5. Magnesium stearate | 1.0 | 1.0 | 1.0 | 2.0 |
| | 130.0 | 130.0 | 130.0 | 180.0 |

| Manufacturing Procedure |
|---|
| 1. Prepare a premix of item 1 with part of item 2. |
| 2. Add the mixture in Step 1 to the mixture of remainder of items 2, 3 and 4 and mix for 10 minutes. Add item 5 and mix for 3 minutes: compress using suitable punch on suitable press. |

EXAMPLE 26

Cream 0.05%

The following is the quantitative composition of drug:

| Ingredients | g/kg | Reasonable Variations |
|---|---|---|
| (5Z,7beta,9alpha, 11alpha,15R,16S)-6,9-epoxy-7,16-difluoro-11,15-dihydroxy prost-5-en-1-oic acid methyl ester | 0.525* | — |
| Glyceryl Monostearate S.E.[1] | 100.00 | 80–120 |
| Polysorbate 60[2] | 20.00 | 15–25 |
| Cetyl Alcohol | 50.00 | 40–60 |
| Petrolatum | 70.00 | 50–90 |
| Methyl Paraben | 1.50 | 1.25–1.75 |
| Propyl Paraben | 0.50 | 0.4–0.6 |
| Propylene Glycol | 200.00 | 150–250 |
| Purified Water | 574.055 | 525–625 |
| Total | 1016.58 gm | |

[1]Arlacel 165
[2]Tween 60
*3% excess of drug

EXAMPLE 27

Cream 0.05%

The following is the quantitative composition of drug:

| Ingredients | g/kg | Reasonable Variations |
|---|---|---|
| (5Z,7beta,9alpha,11alpha,-15R,16S)-6,9-epoxy-7-fluoro-11,15-dihydroxy prost-5-en-1-oic acid methyl ester | 0.525* | — |
| Glyceryl Monostearate S.E.[1] | 100.00 | 80–120 |
| Polysorbate 60[2] | 20.00 | 15–25 |
| Cetyl Alcohol | 50.00 | 40–60 |
| Petrolatum | 70.00 | 50–90 |
| Methyl Paraben | 1.50 | 1.25–1.75 |
| Propyl Paraben | 0.50 | 0.4–0.6 |
| Propylene Glycol | 200.00 | 150–250 |
| Purified Water | 574.055 | 525–625 |
| Total | 1016.58 gm | |

[1]Arlacel 165
[2]Tween 60
*3% excess of drug

EXAMPLE 28

Cream 0.25%

The following is the quantitative composition of drug:

| Ingredients | g/kg | Reasonable Variations |
|---|---|---|
| (5Z,7beta,9alpha, 11alpha,15R,16S)-6,9-epoxy-7,16-difluoro-11,15-dihydroxy prost-5-en-1-oic acid methyl ester | 2.575* | — |
| Glyceryl Monostearate S.E.[1] | 100.00 | 80–120 |

25
-continued

The following is the quantitative composition of drug:

| Ingredients | g/kg | Reasonable Variations |
|---|---|---|
| Polysorbate 60[2] | 20.00 | 15–25 |
| Cetyl Alcohol | 50.00 | 40–60 |
| Petrolatum | 70.00 | 50–90 |
| Methyl Paraben | 1.50 | 1.25–1.75 |
| Propyl Paraben | 0.50 | 0.4–0.6 |
| Propylene Glycol | 200.00 | 150–250 |
| Purified Water | 571.395 | 500–600 |
| Total | 1015.97 gm | |

[1]Arlacel 165
[2]Tween 60
*3% excess of drug

EXAMPLE 29

Cream 0.25%

The following is the quantitative composition of drug:

| Ingredients | g/kg | Reasonable Variations |
|---|---|---|
| (5Z,7beta,9alpha,11alpha,-15R,16S)-6,9-epoxy-7-fluoro-11,15-dihydroxy prost-5-en-1-oic acid methyl ester | 2.575* | — |
| Glyceryl Monostearate S.E.[1] | 100.00 | 80–120 |
| Polysorbate 60[2] | 20.00 | 15–25 |
| Cetyl Alcohol | 50.00 | 40–60 |
| Petrolatum | 70.00 | 50–90 |
| Methyl Paraben | 1.50 | 1.25–1.75 |
| Propyl Paraben | 0.50 | 0.4–0.6 |
| Propylene Glycol | 200.00 | 150–250 |
| Purified Water | 571.395 | 500–600 |
| Total | 1015.97 gm | |

[1]Arlacel 165
[2]Tween 60
*3% excess of drug

EXAMPLE 30

Cream 0.25%

The following is the quantitative composition of drug:

| Ingredients | g/kg | Reasonable Variations |
|---|---|---|
| [5Z,7beta,9alpha,11alpha,15R,16S]-6,9-epoxy-7,16-difluoro-11,15-dihydroxy prosten-5-en-1-oic acid sodium salt | 5.150* | — |
| Glyceryl Monostearate S.E.[1] | 100.00 | 80–120 |
| Polysorbate 60[2] | 20.00 | 15–25 |
| Cetyl Alcohol | 50.00 | 40–60 |
| Petrolatum | 70.00 | 50–90 |
| Methyl Paraben | 1.50 | 1.25–1.75 |
| Propyl Paraben | 0.50 | 0.4–0.6 |
| Propylene Glycol | 200.00 | 150–250 |
| Purified Water | 568.05 | 500–600 |
| Total | 1015.20 gm | |

[2]Arlacel 165
[2]Tween 60
*3% excess of drug

EXAMPLE 31

Cream 0.5%

The following is the quantitative composition of drug:

| Ingredients | g/kg | Reasonable Variations |
|---|---|---|
| (5Z,7beta,9alpha,11alpha,-15R,16S)-6,9-epoxy-7-fluoro-11,15-dihydroxy prost-5-en-1-oic acid methyl ester | 5.150* | — |
| Glyceryl Monostearate S.E.[1] | 100.00 | 80–120 |
| Polysorbate 60[2] | 20.00 | 15–25 |
| Cetyl Alcohol | 50.00 | 40–60 |
| Petrolatum | 70.00 | 50–90 |
| Methyl Paraben | 1.50 | 1.25–1.75 |
| Propyl Paraben | 0.50 | 0.4–0.6 |
| Propylene Glycol | 200.00 | 150–250 |
| Purified Water | 568.05 | 475–575 |
| Total | 1015.20 gm | |

[1]Arlacel 165
[2]Tween 60
*3% excess of drug

We claim:

1. A compound of the formula:

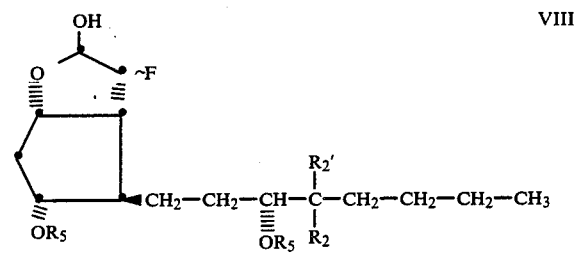

VIII wherein $R_2$ is hydrogen, methyl or fluoro, $R_2'$ is fluoro, hydrogen, trifluoromethyl, or methyl; $R_5$ is tri(lower alkyl)silyl; with the proviso that when $R_2'$ is trifluoromethyl, $R_2$ is hydrogen or methyl; optical antipodes or racemates thereof.

2. The compound of claim 1 which is [3S-[3alpha,3a alpha,4alpha(3S*),5beta,6a alpha]]-hexahydro-3-fluoro-5-[[(1,1-dimethylethyl)dimethylsilyl)oxy]-4-[3-[[(1,1-dimethylethyl)dimethylsilyl]oxy]octyl]-2H-cyclopenta[b]furan-2-ol.

3. The compound of claim 1 which is [3S-[3alpha,3a alpha,4alpha(3R*,4S*),5beta,6a alpha)]-hexahydro-3-fluoro-5-[[(1,1-dimethylethyl)dimethylsilyl]oxy]-4-[[[3-(1,1-dimethylethyl)dimethylsilyl]oxy]-4-fluorooctyl]-2H-cyclopenta[b]furan-2-ol.

4. A compound of the formula:

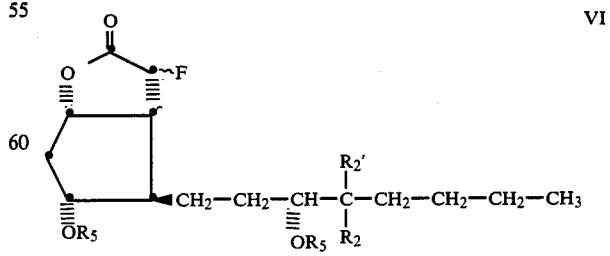

VI wherein $R_2$ is methyl, hydrogen or fluoro; $R_2'$ is fluoro, hydrogen, trifluoromethyl or methyl; $R_5$ is tri(lower alkyl silyl); and with the proviso that when R₂' is trifluoromethyl, R₂ is hydrogen or methyl;

optical antipodes and racemates thereof.

5. The compound of claim 4 which is [3S-[3alpha,3a alpha,4alpha(3S*),5beta,6a alpha]]-hexahydro-3-fluoro-5-[[(1,1-dimethylethyl)dimethylsilyl]]oxy-4-[[[3-(1,1-dimethylethyl)dimethylsilyl]oxy]octyl]-2H-cyclopenta[b]furan-2-one.

6. The compound of claim 4 which is [3S-[3alpha,3a alpha,4alpha(3R*,4S*),5beta,6a alpha]]-hexahydro-3-fluoro-5-[[(1,1-dimethylethyl)dimethylsilyl]]oxy]-4-[[[3-(1,1-dimethylethyl)dimethylsilyl]oxy]-4-fluorooctyl]-2H-cyclopenta[b]furan-2-one.

7. A compound of the formula:

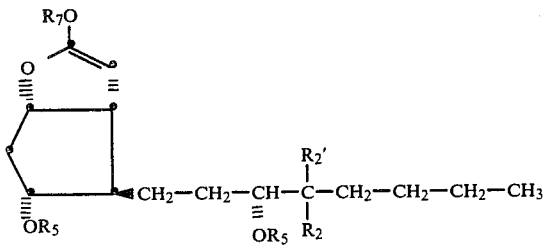

wherein R₅ and R₇ are tri(lower alkyl)silyl; R₂' is fluoro, hydrogen, trifluoromethyl, or methyl; R₂ is hydrogen, methyl or fluoro; with the proviso that when R₂' is trifluoromethyl, R₂ is hydrogen or methyl, optical antipodes and racemates thereof.

8. The compound of claim 1 which is [3aR-[3a alpha,4alpha(3R*),5beta,6a alpha]]-4,5,6,6a-tetrahydro-5-[[1,1-dimethylethyl)dimethylsilyl]oxy]-4-[3-[1,1-dimethylethyl)dimethylsilyl]oxy]-octyl-2-[(trimethylsilyl)oxy]-3aH-cyclopenta[b]furan.

* * * * *